US012747434B2

(12) United States Patent
Kim et al.

(10) Patent No.: US 12,747,434 B2
(45) Date of Patent: Sep. 29, 2026

(54) **RECOMBINANT YEAST *SACCHAROMYCES BOULARDII* FOR PRODUCING NEOAGAROOLIGOSACCHARIDES AND USE THEREOF**

(71) Applicant: KOREA UNIVERSITY RESEARCH AND BUSINESS FOUNDATION, Seoul (KR)

(72) Inventors: Kyoung Heon Kim, Seoul (KR); So Ra Yu, Seoul (KR); Ye Rin Jin, Seoul (KR); Eun Ju Yun, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 358 days.

(21) Appl. No.: 18/571,437

(22) PCT Filed: Jun. 20, 2022

(86) PCT No.: PCT/KR2022/008703
§ 371 (c)(1),
(2) Date: Feb. 27, 2024

(87) PCT Pub. No.: WO2022/265470
PCT Pub. Date: Dec. 22, 2022

(65) Prior Publication Data

US 2024/0294891 A1 Sep. 5, 2024

(30) Foreign Application Priority Data

Jun. 18, 2021 (KR) ........................ 10-2021-0079055

(51) Int. Cl.
*C12N 9/38* (2006.01)
*C12N 15/81* (2006.01)
*C12P 19/02* (2006.01)
*C12P 19/14* (2006.01)

(52) U.S. Cl.
CPC ........... *C12N 9/2468* (2013.01); *C12N 15/81* (2013.01); *C12P 19/02* (2013.01); *C12P 19/14* (2013.01); *C12Y 302/01081* (2013.01)

(58) Field of Classification Search
CPC .................................................... C12N 9/2468
See application file for complete search history.

(56) References Cited

U.S. PATENT DOCUMENTS

2020/0360447 A1* 11/2020 Kim ...................... A23L 33/135
2021/0317492 A1* 10/2021 Kim ..................... C07D 307/20

FOREIGN PATENT DOCUMENTS

KR 10-2011-0093120 A 8/2011
KR 10-2014-0048516 A 4/2014
KR 10-2014-0060045 A 5/2014
KR 10-2018-0007725 A 1/2018
KR 10-2018-0115040 A 10/2018
KR 10-2020-0028553 A 3/2020
WO WO-2019098708 A1 * 5/2019 ........... A23L 33/135
WO WO-2020050663 A1 * 3/2020 ........... C07D 307/20

OTHER PUBLICATIONS

Jing-Jing Liu et al., "Metabolic Engineering of Probiotic *Saccharomyces boulardii*", Applied and Environmental Microbiology, vol. 82, No. 8, 2016, pp. 2280-2287.
Deniz Durmusoglu et al., "Establishing probiotic *Saccharomyces boulardii* as a model organism for synthesis and delivery of biomolecules", bioRxiv, https://doi.org/10.1101/2020.01.22.915389, 2020, pp. 1-56.
Deniz Durmusoglu et al., "In Situ Biomanufacturing of Small Molecules in the Mammalian Gut by Probiotic *Saccharomyces boulardii*", ACS Synthetic Biology, vol. 10, 2021, pp. 1039-1052.
Yerin Jin et al., "Production of neoagarooligosaccharides by probiotic yeast *Saccharomyces cerevisiae* var. *boulardii* engineered as a microbial cell factory", Microbial Cell Factories, vol. 20, No. 160, 2021, pp. 1-10.
Korean Office Action for KR 10-2021-0079055 dated May 18, 2023.
International Search Report for PCT/KR2022/008703 dated Oct. 5, 2022.

* cited by examiner

*Primary Examiner* — Robert J Yamasaki
(74) *Attorney, Agent, or Firm* — Sughrue Mion, PLLC

(57) ABSTRACT

The present invention relates to a strain that produces neoagarooligosaccharides from agarose, which is a representative polysaccharide constituting red algae, using *Saccharomyces boulardii*, which is a probiotic yeast, a production method thereof, and a use thereof. The present invention aims to achieve synbiotics through the production of prebiotic substances using probiotic strains and can be used as an intestinal microbial factory.

6 Claims, 6 Drawing Sheets

Specification includes a Sequence Listing.

FIG.4 (A)
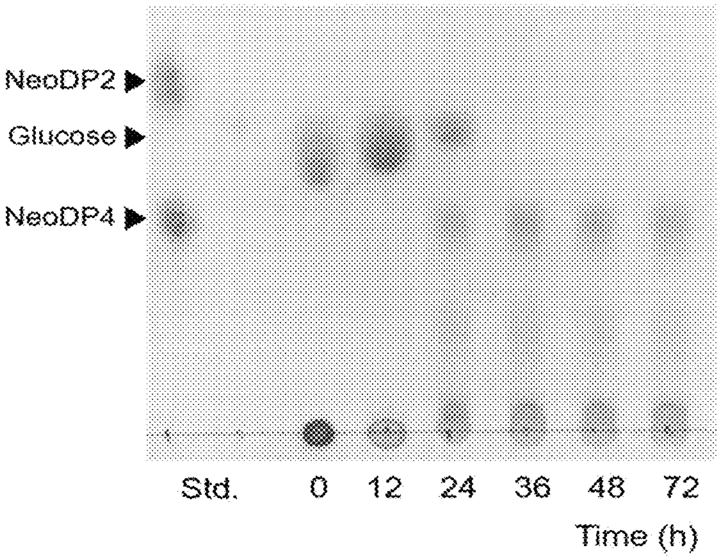
FIG.4 (B)
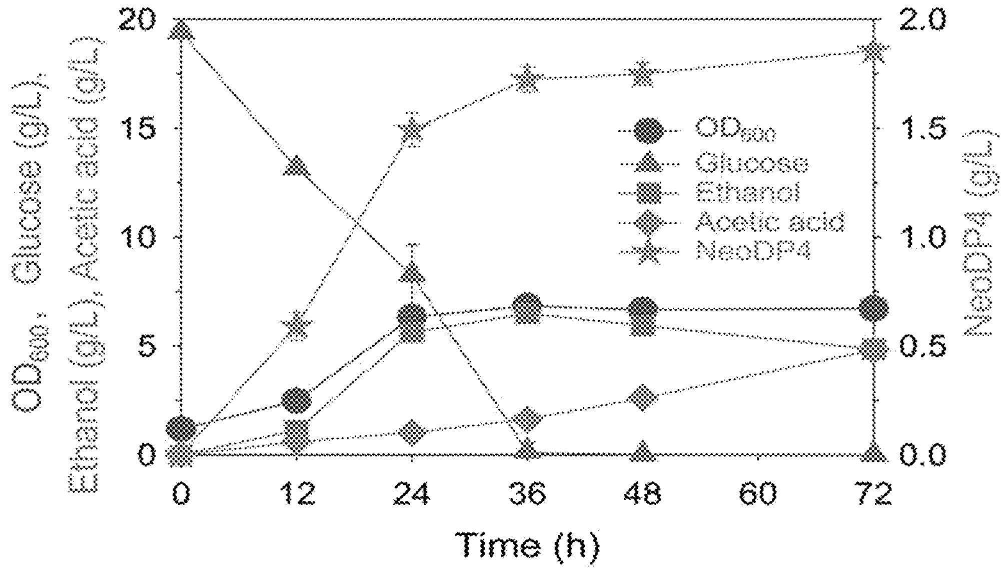

SEQUENCE LISTING

```
<160> NUMBER OF SEQ ID NOS: 31

<210> SEQ ID NO 1
<211> LENGTH: 894
<212> TYPE: DNA
<213> ORGANISM: Artificial Sequence
<220> FEATURE:
<223> OTHER INFORMATION: BpGH16A coding sequence

<400> SEQUENCE: 1

gcagaaaatt taaataataa atcatacgag tgggacatct atcctgtacc agctaatgct     60
```

```
ggtgacggta tggtgtggaa acttcatcca cagtcggacg actttaatta tattgctgac    120

gaaaaggata aaggaaaaga gttctatgcc aaatggactg atttctatca taatcattgg    180

acagggcctg ctcctacaat atggcagaga gaccatgttt ccgtttcaga cggattcctt    240

aaaatcagag ccagccgtcc tgaagatgtc cctctaaaga aagttgtaag cggacctaac    300

acaaaggaac tcccgggaac ctatacagga tgtattacat cgaagactcg tgtaaaatat    360

ccggtttatg tagaagcata cgccaaactt tcaaattcaa ccatggcatc cgatgtatgg    420

atgcttagcc ctgatgatac tcaggaaatc gatattatag aggcatacgg tggtgataga    480

gacggtggag gttatggtgc cgacagactt cacttaagcc atcacatatt catccgtcag    540

ccattcaagg attatcagcc aaaggattca ggttcatggt ataaggatga caagggaaca    600

ttgtggcgcg atgattttca tcgtgttgga gtattctgga aagatccttt cacacttgaa    660

tattatgtag atggagaact cgtcagaact ataagcggta aggatattat tgatcccaac    720

aactacactg gtggcacggg gttggttaag gatatggaca tcataataaa tatggaagac    780

caaagctgga gggccgttaa aggtttaagc cctacggatg aggaactgaa aaatgtggaa    840

gatcacactt tccttgtcga ctggataagg gtttatacac tggtcccaga agaa          894


<210> SEQ ID NO 2
<211> LENGTH: 54
<212> TYPE: DNA
<213> ORGANISM: Artificial Sequence
<220> FEATURE:
<223> OTHER INFORMATION: CL signal paptide  coding sequence

<400> SEQUENCE: 2

atgaggtctt tgctaatctt ggtgctttgc ttcctgcccc tggctgctct gggg           54


<210> SEQ ID NO 3
<211> LENGTH: 267
<212> TYPE: DNA
<213> ORGANISM: Artificial Sequence
<220> FEATURE:
<223> OTHER INFORMATION: alpha-MF signal paptide  coding sequence

<400> SEQUENCE: 3

atgagatttc cttcaatttt tactgctgtt ttattcgcag catcctccgc attagctgct     60

ccagtcaaca ctacaacaga agatgaaacg gcacaaattc cggctgaagc tgtcatcggt    120

tactcagatt tagaagggga tttcgatgtt gctgttttgc cattttccaa cagcacaaat    180

aacgggttat tgtttataaa tactactatt gccagcattg ctgctaaaga agaaggggta    240

tctctcgaga aaagagaggc tgaagct                                        267


<210> SEQ ID NO 4
<211> LENGTH: 1074
<212> TYPE: DNA
<213> ORGANISM: Artificial Sequence
<220> FEATURE:
<223> OTHER INFORMATION: STA1 signal paptide  coding sequence

<400> SEQUENCE: 4

atggtaggcc tcaaaaatcc atatacgcac actatgcaaa gaccatttct actcgcttat     60

ttggtccttt cgcttctatt taactcagct ttgggttttc caactgcact agttcctaga    120

ggatcctcct ctagcaacat cacttcctcc ggtccatctt caactccatt cagctctgct    180

actgaaagct tttctactgg cactactgtc actccatcat catccaaata ccctggcagt    240
```

```
aaaacagaaa cttctgtttc ttctacaacc gaaactacca ttgttccaac tacaactacg    300

acttctgtca taacaccatc aacaaccact attaccacta cggtttgctc tacaggaaca    360

aactctgccg gtgaaactac ttctggatgc tctccaaaga ccattacaac tactgttcca    420

tgttcaacca gtccaagcga aaccgcatcg gaatcaacaa ccacttcacc taccacacct    480

gtaactacag ttgtctcaac caccgtcgtt actactgagt attctactag tacaaaacaa    540

ggtggtgaaa ttacaactac atttgtcacc aaaaacattc caaccactta cctaactaca    600

attgctccaa cttcatcagt cactacggtt accaatttca ccccaaccac tattactact    660

acggtttgct ctacaggaac aaactctgcc ggtgaaacta cctctggatg ctctccaaag    720

actgtcacaa caactgttcc ttgttcaact ggtactggcg aatacactac tgaagctacc    780

gcccctgtta caacagctgt cacaaccacc gttgttacca ctgaatcctc tacgggtact    840

aactccgctg gtaagacgac aactagttac acaacaaagt ctgtaccaac cacctatgta    900

tttgactttg gcaagggcat tctcgatcaa agctgcggcg gtgtattttc aaacaacggc    960

tcttcgcaag tgcagctgcg ggatgtagtc ttgatgaatg ggacagtggt atacgattca   1020

aacggcgctt gggacagtag tgcgctggag gagtggctcc agcgacagaa aaaa         1074


<210> SEQ ID NO 5
<211> LENGTH: 57
<212> TYPE: DNA
<213> ORGANISM: Artificial Sequence
<220> FEATURE:
<223> OTHER INFORMATION: SED1 signal paptide coding sequence

<400> SEQUENCE: 5

atgaaattat caactgtcct attatctgcc ggtttagcct cgactacttt ggcccaa        57


<210> SEQ ID NO 6
<211> LENGTH: 20
<212> TYPE: DNA
<213> ORGANISM: Artificial Sequence
<220> FEATURE:
<223> OTHER INFORMATION: gHIS3_F

<400> SEQUENCE: 6

tccacctagc ggatgactct                                                 20


<210> SEQ ID NO 7
<211> LENGTH: 20
<212> TYPE: DNA
<213> ORGANISM: Artificial Sequence
<220> FEATURE:
<223> OTHER INFORMATION: gHIS3_R

<400> SEQUENCE: 7

tgcattacct tgtcatcttc                                                 20


<210> SEQ ID NO 8
<211> LENGTH: 60
<212> TYPE: DNA
<213> ORGANISM: Artificial Sequence
<220> FEATURE:
<223> OTHER INFORMATION: dDNA_HIS3_F

<400> SEQUENCE: 8

gtaaagcgta ttacaaatga aaccaagatt cagattgcga tctctttaaa gggttaaccc     60


<210> SEQ ID NO 9
<211> LENGTH: 60
```

<212> TYPE: DNA
<213> ORGANISM: Artificial Sequence
<220> FEATURE:
<223> OTHER INFORMATION: dDNA_HIS3_R

<400> SEQUENCE: 9
ttctgggaag atcgagtgct ctatcgctag gggttaaccc tttaaagaga tcgcaatctg 60

<210> SEQ ID NO 10
<211> LENGTH: 41
<212> TYPE: DNA
<213> ORGANISM: Artificial Sequence
<220> FEATURE:
<223> OTHER INFORMATION: 16A_W/OSP_F_SpeI

<400> SEQUENCE: 10
ataactagtg cagaaaattt aaataataaa tcatacgagt g 41

<210> SEQ ID NO 11
<211> LENGTH: 33
<212> TYPE: DNA
<213> ORGANISM: Artificial Sequence
<220> FEATURE:
<223> OTHER INFORMATION: 16A_W/OSP_R_XhoI

<400> SEQUENCE: 11
atactcgagt tcttctggga ccagtgtata aac 33

<210> SEQ ID NO 12
<211> LENGTH: 90
<212> TYPE: DNA
<213> ORGANISM: Artificial Sequence
<220> FEATURE:
<223> OTHER INFORMATION: 16A_CL_F_SpeI

<400> SEQUENCE: 12
ataactagta tgaggtcttt gctaatcttg gtgctttgct tcctgcccct ggctgctctg 60
ggggcagaaa atttaaataa taaatcatac 90

<210> SEQ ID NO 13
<211> LENGTH: 25
<212> TYPE: DNA
<213> ORGANISM: Artificial Sequence
<220> FEATURE:
<223> OTHER INFORMATION: 16A_CL_R_XhoI

<400> SEQUENCE: 13
atactcgagt tcttctggga ccagt 25

<210> SEQ ID NO 14
<211> LENGTH: 34
<212> TYPE: DNA
<213> ORGANISM: Artificial Sequence
<220> FEATURE:
<223> OTHER INFORMATION: alpha-MF_F_SpeI

<400> SEQUENCE: 14
ataactagta tgagatttcc ttcaattttt actg 34

<210> SEQ ID NO 15
<211> LENGTH: 40
<212> TYPE: DNA
<213> ORGANISM: Artificial Sequence
<220> FEATURE:
<223> OTHER INFORMATION: alpha-MF_R_16A

<400> SEQUENCE: 15
gcagaaaatt taaataataa agcttcagcc tctcttttct 40

<210> SEQ ID NO 16
<211> LENGTH: 49
<212> TYPE: DNA
<213> ORGANISM: Artificial Sequence
<220> FEATURE:
<223> OTHER INFORMATION: 16A_F_ alpha-MF

<400> SEQUENCE: 16
gagaaaagag aggctgaagc tgcagaaaat ttaaataata aatcatacg 49

<210> SEQ ID NO 17
<211> LENGTH: 29
<212> TYPE: DNA
<213> ORGANISM: Artificial Sequence
<220> FEATURE:
<223> OTHER INFORMATION: 16A_R_alpha-MF_BamHI

<400> SEQUENCE: 17
ataggatcct tcttctggga ccagtgtat 29

<210> SEQ ID NO 18
<211> LENGTH: 28
<212> TYPE: DNA
<213> ORGANISM: Artificial Sequence
<220> FEATURE:
<223> OTHER INFORMATION: STA1_F_EcoRI

<400> SEQUENCE: 18
atagaattca tggtaggcct caaaaatc 28

<210> SEQ ID NO 19
<211> LENGTH: 49
<212> TYPE: DNA
<213> ORGANISM: Artificial Sequence
<220> FEATURE:
<223> OTHER INFORMATION: STA1_16A_ R

<400> SEQUENCE: 19
gcagaaaatt taaataataa atcatacgag ttttttctgt cgctggagc 49

<210> SEQ ID NO 20
<211> LENGTH: 50
<212> TYPE: DNA
<213> ORGANISM: Artificial Sequence
<220> FEATURE:
<223> OTHER INFORMATION: 16A_STA1_ F

<400> SEQUENCE: 20
ggctccagcg acagaaaaaa gcagaaaatt taaataataa atcatacgag 50

<210> SEQ ID NO 21
<211> LENGTH: 29
<212> TYPE: DNA
<213> ORGANISM: Artificial Sequence
<220> FEATURE:
<223> OTHER INFORMATION: 16A_ R_XhoI

<400> SEQUENCE: 21
atactcgagt tcttctggga ccagtgtat 29

<210> SEQ ID NO 22
<211> LENGTH: 89

<212> TYPE: DNA
<213> ORGANISM: Artificial Sequence
<220> FEATURE:
<223> OTHER INFORMATION: 16A_SED1_F_SpeI

<400> SEQUENCE: 22
ataactagta tgaaattatc aactgtccta ttatctgccg gtttagcctc gactactttg 60
gcccaagcag aaaatttaaa taataaatc 89

<210> SEQ ID NO 23
<211> LENGTH: 24
<212> TYPE: DNA
<213> ORGANISM: Artificial Sequence
<220> FEATURE:
<223> OTHER INFORMATION: 16A_SED1_R_XhoI

<400> SEQUENCE: 23
atactcgagt tcttctggga ccag 24

<210> SEQ ID NO 24
<211> LENGTH: 71
<212> TYPE: DNA
<213> ORGANISM: Artificial Sequence
<220> FEATURE:
<223> OTHER INFORMATION: dDNA-CS5-F

<400> SEQUENCE: 24
aaaagagaag aaaaaagaga agaaatgaat tctattatga tagcgaatgc aattaaccct 60
cactaaaggg a 71

<210> SEQ ID NO 25
<211> LENGTH: 72
<212> TYPE: DNA
<213> ORGANISM: Artificial Sequence
<220> FEATURE:
<223> OTHER INFORMATION: dDNA-CS5-R

<400> SEQUENCE: 25
tgctggttgc cttattaatt tatatggaag acgagataat tcattaatta gtaatacgac 60
tcactatagg gc 72

<210> SEQ ID NO 26
<211> LENGTH: 90
<212> TYPE: DNA
<213> ORGANISM: Artificial Sequence
<220> FEATURE:
<223> OTHER INFORMATION: dDNA-CS5+60_F

<400> SEQUENCE: 26
atggtacacg ctcttggcaa cattgaaatt acagctctca tatataaaaa atggaaagaa 60
aaaagagaag aaaaaagaga agaaatgaat 90

<210> SEQ ID NO 27
<211> LENGTH: 90
<212> TYPE: DNA
<213> ORGANISM: Artificial Sequence
<220> FEATURE:
<223> OTHER INFORMATION: dDNA-CS5+60_R

<400> SEQUENCE: 27
ggcataacaa tagcgcacag atccgcaggt ttcgtaatac gcttaacaat aggcgtctcc 60
tgctggttgc cttattaatt tatatggaag 90

-continued

```
<210> SEQ ID NO 28
<211> LENGTH: 43
<212> TYPE: DNA
<213> ORGANISM: Artificial Sequence
<220> FEATURE:
<223> OTHER INFORMATION: gCS5_F

<400> SEQUENCE: 28

ctggtagttg cacagaaaga gttttagagc tagaaatagc aag                    43


<210> SEQ ID NO 29
<211> LENGTH: 42
<212> TYPE: DNA
<213> ORGANISM: Artificial Sequence
<220> FEATURE:
<223> OTHER INFORMATION: gCS5_R

<400> SEQUENCE: 29

tctttctgtg caactaccag cgatcattta tctttcactg cg                     42


<210> SEQ ID NO 30
<211> LENGTH: 27
<212> TYPE: DNA
<213> ORGANISM: Artificial Sequence
<220> FEATURE:
<223> OTHER INFORMATION: Conf-CS5-F

<400> SEQUENCE: 30

aatgaattct attatgatag cgaatgc                                      27


<210> SEQ ID NO 31
<211> LENGTH: 19
<212> TYPE: DNA
<213> ORGANISM: Artificial Sequence
<220> FEATURE:
<223> OTHER INFORMATION: Conf-CS5-R

<400> SEQUENCE: 31

cacaggattt acgaagacc                                               19
```

RECOMBINANT YEAST *SACCHAROMYCES BOULARDII* FOR PRODUCING NEOAGAROOLIGOSACCHARIDES AND USE THEREOF

CROSS REFERENCE TO RELATED APPLICATIONS

This application is a National Stage of International Application No. PCT/KR2022/008703 filed Jun. 20, 2022, claiming priority based on Korean Patent Application No. 10-2021-0079055 filed Jun. 18, 2021, the entire disclosures of which are incorporated herein by reference.

BACKGROUND

1. Field of the Invention

The present invention relates to a recombinant strain that produces neoagarooligosaccharids from agarose, which is a representative polysaccharide constituting red algae, and a use thereof.

2. Discussion of Related Art

*Saccharomyces boulardii* is a generally recognized as safe (GRAS) non-pathogenic yeast first discovered in the peels of lychee and mangosteen. It is known that *Saccharomyces boulardii* can survive in the human gastrointestinal tract due to its high tolerance to low pH and heat (Douradinha B., et al. (2014) Bioengineered. 5, 21-29, Czerucka D., et al. al. (2007) Aliment. Pharmacol. Ther. 26(6), 767-78). *Saccharomyces boulardii* is the only probiotic yeast found to be effective in double-blind studies.

Unlike digestible food, non-digestible food reaches the large intestine and is utilized by the intestinal microbial community. As a result, non-digestible food changes the intestinal environment and affects overall human health (Pistollato F., et al. (2016) Nutr Rev. 74, 624-634, Sonnenburg E. D., et al. (2014) Cell Metab. 20, 779-786). Agarose, which is a representative polysaccharide constituting red algae, is one of the non-digestible foods commonly found in East Asia (Kolb N., et al. (2004) Food Technol Biotechnol. 42, 57-61). Agarose is decomposed into neoagarooligosaccharides such as neoagarotetraose and neoagarobiose by endo-type beta-agarase, and the neoagarooligosaccharides have been reported to have various physiological and biological functions such as anti-obesity, anti-diabetic, anti-inflammatory, anti-tumor activity, and prebiotic effects (Torres M. D., et al. (2019) Mar Drugs. 17, 314, Hong S. J., et al. (2017) Mar Drugs. 15, 90, Lee M. H., et al. (2017) BMB Rep. 50, 263, Lin F., et al. (2019) Mar Drugs. 17, 154, Wang W., et al. (2017) Sci Rep. 7, 442-52, Kim M., et al. (2020) Biomaterials. 263, 120391, Hu G., et al. (2006) Anaerobe. 12, 260-266). In particular, the tetrasaccharide neoagarotetraose, which is a type of neoagarooligosaccharide, was also found to have various functional properties such as anti-inflammatory and antioxidant activity, and prebiotic effects (Zhang N., et al. (2017) Food Agric Immunol. 28, 1408-1423, Xu X-Q., et al. (2018) Food Chem. 240, 330-337).

At this time, when an intestinal microbial factory that can produce useful proteins such as prebiotics directly in the intestines is developed, more accurate research on the impact of intestinal microorganisms on health will become possible, and furthermore, it may be used to treat actual diseases.

However, there have been no reports of successful research in producing neoagarooligosaccharides that can be used as prebiotics from red algae agar or agarose in the yeast *Saccharomyces boulardii*, which is a eukaryotic cell and a probiotic.

RELATED ART DOCUMENT

Patent Document

Korean Patent Registration No. 10-1864800

SUMMARY OF THE INVENTION

The present invention is directed to providing a probiotic recombinant yeast capable of producing prebiotic substances in the intestines.

The present invention is also directed to providing a composition for producing a prebiotic including a probiotic recombinant yeast and a substrate, and a production method thereof.

In order to produce prebiotic substances from probiotic yeast using metabolic engineering technology, the present inventors attempted to produce neoagarooligosaccharides including neoagarotetraose for the first time by introducing a *Bacteroides* plebeius-derived enzyme BpGH16A gene into the yeast *Saccharomyces boulardii*. The present inventors completed the present invention by quantifying neoagarooligosaccharides produced after fermenting *Saccharomyces boulardii* with agarose using a method of quantifying neoagarooligosaccharides utilizing high-performance liquid chromatography (HPLC) and preparing *Saccharomyces boulardii*, which is a probiotic yeast that can express BpGH16A, which is a beta-agarase, and secrete the enzyme outside the strain.

Accordingly, the present invention provides recombinant *Saccharomyces boulardii* transformed with a gene encoding beta-agarase.

The purpose of the recombinant *Saccharomyces boulardii* of the present invention is to ultimately use it to produce neoagarooligosaccharides using agarose as a substrate. However, since *Saccharomyces boulardii* cannot absorb agarose as a substrate into the strain and metabolize it, a means is required to secrete the beta-agarase enzyme, which can decompose agarose into neoagarooligosaccharides, outside the strain. Therefore, the recombinant *Saccharomyces boulardii* of the present invention may be transformed with a gene encoding a signal peptide capable of secreting the beta-agarase outside the strain.

The signal peptide plays a role in secreting beta-agarase, specifically an enzyme expressed from the BpGH16A gene represented by SEQ ID NO: 1 in *Saccharomyces boulardii*, and may be one or more of a chicken lysozyme signal peptide (CL), a *Saccharomyces cerevisiae*-derived α-binding factor signal peptide (α-MF), a *Saccharomyces diastaticus*-derived STA1 signal peptide (STA1), and a *Saccharomyces cerevisiae*-derived SED1 signal peptide (SED1). In one specific example, it was confirmed that when SED1 was used as the signal peptide, a secretion amount of enzyme and a production amount of neoagarooligosaccharides were the best.

The chicken lysozyme signal peptide (CL) may be represented by SEQ ID NO: 2, the *Saccharomyces cerevisiae*-derived α-binding factor signal peptide (α-MF) may be represented by SEQ ID NO: 3, the *Saccharomyces diastaticus*-derived STA1 signal peptide (STA1) may be represented by SEQ ID NO: 4, and the *Saccharomyces cerevisiae*-derived SED1 signal peptide (SED1) may be represented by SEQ ID NO: 5.

The transformation of *Saccharomyces boulardii* with a gene encoding the beta-agarase and/or signal peptide can be performed using a recombinant vector including the gene or CRISPR-Cas9, which is a genetic recombination technology.

When using a recombinant vector such as a plasmid for the transformation of the *Saccharomyces boulardii*, auxotrophic mutants, for example, a mutant *Saccharomyces boulardii* strain in which one or more of the HIS3, TRP1 and URA3 genes are inactivated may be used.

In addition, the present invention provides a composition for producing prebiotics including the recombinant *Saccharomyces boulardii* and agarose as a substrate.

The recombinant *Saccharomyces boulardii* of the present invention can produce prebiotics by secreting beta-agarase outside the strain and decomposing agarose as a substrate, and in addition, *Saccharomyces boulardii* is a probiotic strain and may provide prebiotics and probiotics at the same time.

Accordingly, the present invention provides a synbiotic composition including the recombinant *Saccharomyces boulardii* and agarose as a substrate.

The prebiotics may be neoagarooligosaccharides, and specifically, may be neoagarobiose, neoagarotetraose, and neoagarohexaose, which are produced through the decomposition of agarose.

In addition, the composition may further include other probiotics in addition to the *Saccharomyces boulardii* strain, specifically, may include strains belonging to the *Lactobacillus* genus, *Bifidobacterium* genus, and *Enterococcus* genus, and more specifically, may include any probiotic strain that can ingest and metabolize neoagarooligosaccharides without limitation.

In addition, the present invention includes a method of producing neoagarooligosaccharides, including: reacting the culture fluid or extract of the recombinant *Saccharomyces boulardii* with agarose as a substrate; and separating and purifying neoagarooligosaccharides from the product of the above step The description of the recombinant *Saccharomyces boulardii* and neoagarooligosaccharide is omitted to prevent duplication with the above-mentioned content.

Specifically, the culture or fermentation of the strain to produce beta-agarase from the recombinant *Saccharomyces boulardii* of the present invention is performed at a temperature of 20 to 40° C., preferably 30 to 40° C. for 1 to 7 days, preferably for 2 to 5 days.

BRIEF DESCRIPTION OF THE DRAWINGS

FIG. 2(B) is the result of fermentation product analysis using a strain (SB-HTU_16A_C) into which the BpGH16A gene and a chicken lysozyme signal peptide sequence were introduced. Neoagarotetraose (NeoDP4) was detected as a peak at a retention time of approximately 7.6 minutes.

FIG. 3(A) is the result of analyzing the fermentation product using TLC, and FIG.3(B) is the result of analyzing the fermentation product using HPLC and calculating the concentration.

FIG. 4(A) and FIG. 4(B) show the results of confirming the materials and cell growth generated over time when fermentation was performed at 37° C. for 72 hours using agarose as a substrate using yeast (SB-HTU_16A_D) prepared based on a plasmid. FIG. 4(A) is the result of analyzing fermentation products for 72 hours using TLC. FIG. 4(B) shows the results of HPLC analysis and quantification of cell density and concentrations of glucose, ethanol, acetic acid, and neoagarotetraose during fermentation for 72 hours.

FIG. 5(A) is an overall schematic diagram of the process of introducing beta-agarase into a strain using a CRISPR-Cas9 system. FIG. 5(B) is the result of introducing beta-agarase into the strain using the CRISPR-Cas9 system and then confirming through colony PCR whether it was actually introduced.

FIG 6(A) is the result of analyzing fermentation products for 72 hours using TLC. FIG. 6(B) shows the results of HPLC analysis of cell density and concentrations of glucose, acetic acid, ethanol, and neoagarotetraose during fermentation for 72 hours.

DETAILED DESCRIPTION OF EXEMPLARY EMBODIMENTS

Figure 1:
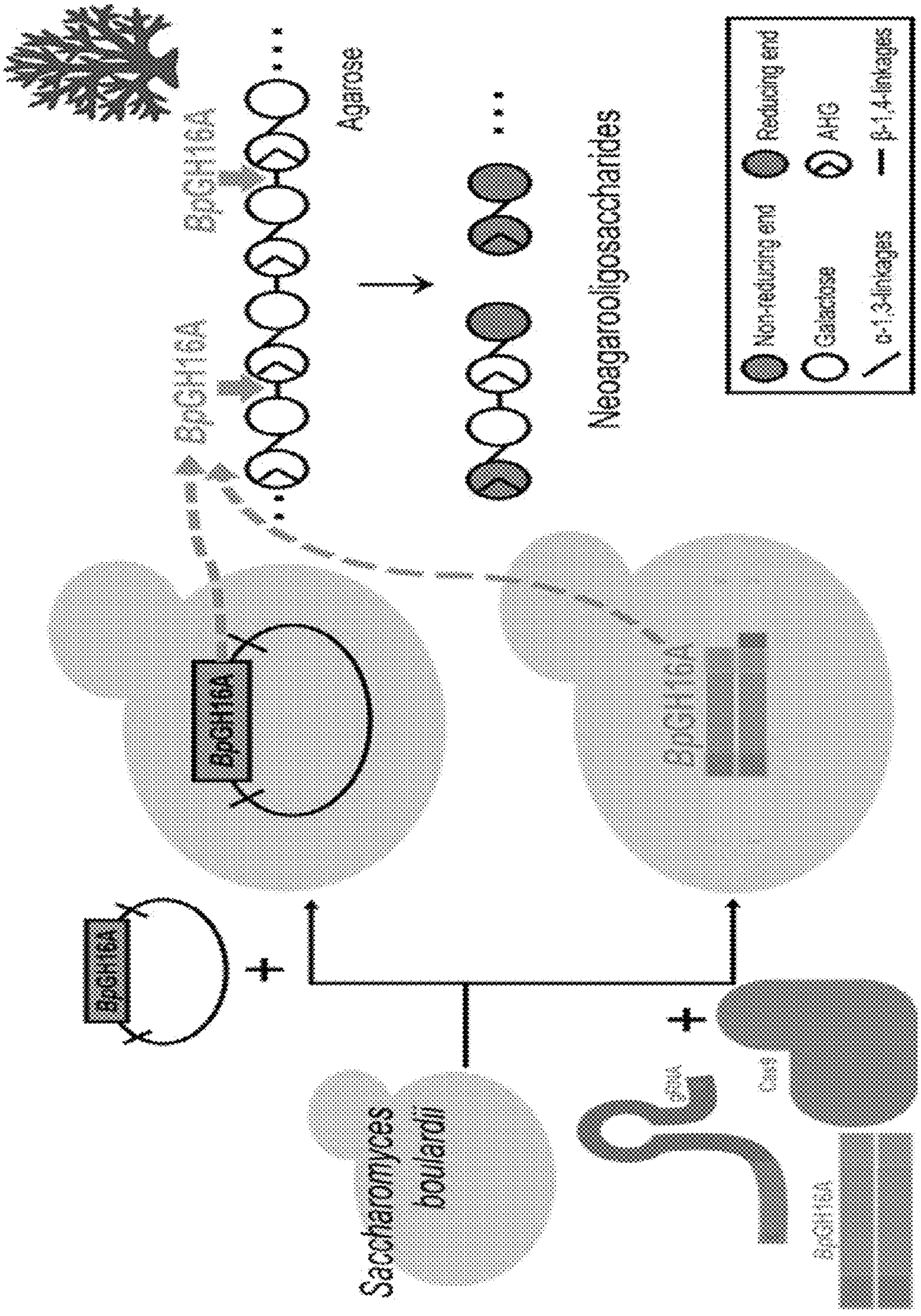
FIG. 1 shows an overall schematic diagram of neoagarotetraose production by *Saccharomyces boulardii* engineered using metabolic engineering technology. The introduction of a BpGH16A gene, which is a beta-agarase, was performed using two different systems: a vector system with an auxotrophic marker and a CRISPR-Cas9 system.

Hereinafter, the present invention will be described in detail by way of Examples. The following Examples merely illustrate the present invention but do not limit the scope of the present invention.

Example 1: Method of Preparing Plasmids and Strains

To use auxotrophic markers during strain production, strains with inactivated HIS3, TRP1, and URA3 genes were generated. The HIS3 gene was inactivated based on strain SB-TU in which TRP1 and URA3 were inactivated (Liu J-J., et al. (2016) Appl Environ Microbiol. 82, 2280-2287). The HIS3 gene was amplified using the primer pair gHIS3_F and gHIS3_R (Table 1), the resulting PCR product was digested by SacI and NotI, and ligated into the pRS42H vector to generate plasmid p42H_gHIS3 (Table 2). The repair DNA required after HIS3 inactivation was amplified by PCR using primers dDNA_HIS3_F and dDNA_HIS3_R (Table 1). Yeast transformation was performed using the PEG-LiAc method (Gietz R. D., et al. (1995) Yeast. 11, 335-360). After yeast transformation, *Saccharomyces boulardii* strain SB-HTU, in which HIS3, TRP1, and URA3 genes were inactivated, was prepared and used in the experiment (Table 3).

Plasmid construction to select an optimal signal peptide for beta-agarase secretion was performed as follows. The gene BACPLE_01670 encoding BpGH16A was cloned into the pRS426GPD plasmid. The BpGH16A gene fragment was amplified by PCR from genomic DNA of *Bacteroides* plebeius DSM 17135 (DSMZ, Braunschweig, Germany) using different primer pairs depending on the type of signal peptide (Table 1). A signal peptide sequence predicted at the N-terminus of BpGH16A was removed and then used. A total of four signal peptides, including a chicken lysozyme signal peptide (CL), a *Saccharomyces cerevisiae*-derived α-binding factor signal peptide (α-MF), a *Saccharomyces diastaticus*-derived STA1 signal peptide (STA1), and a *Saccharomyces cerevisiae*-derived SED1 signal peptide (SED1), were compared (Liu J-J., et al. (2016) Appl Environ Microbiol. 82, 2280-2287, Inokuma K., et al. (2016) Biotechnol Bioeng. 113, 2358-2366, Yanagisawa M., et al. (2016) Enzyme Microb Technol. 85, 82-89). In addition, to construct a control strain without a signal peptide, PCR was performed using the primer pair 16A_W/OSP_F_Spel and 16A_W/OSP_R_Xhol (Table 1). Plasmids such as p426_Bp_W/OSP, p426_Bp_CL, p426_Bp_aMF, p426_Bp_STA1, and p426_Bp_SED1 were generated, and yeast transformation using SB-HTU was performed using the PEG-LiAc method. That is, strains SB-HTU_16A_C, SB-HTU_16A_A, SB-HTU_16A_S, and SB-HTU_16A_D were prepared for a signal peptide comparison experiment (Table 3). As a control strain, SB-HTU_E, which includes only the pRS426GPD vector without BpGH16A and a signal peptide, and SB-HTU_W, which includes the BpGH16A gene but no signal peptide, were prepared and used.

For stable expression of BpGH16A, guide RNA plasmid p42K_CS5 was used to integrate the BpGH16A gene into the genome of *Saccharomyces boulardii* (Table 2). p42K_CS5 was generated by inverse PCR of the pRS42K plasmid including a guide RNA sequence using the primer pair gRNA_CS5_F and gRNA_CS5_R (Table 1). The 20-bp targeting sequence of the guide RNA binds to the front of the PAM sequence (NGG) at an empty locus on chromosome XV (CS5). BpGH16A and SED1 signal peptides were integrated by homologous recombination without affecting the function of other genes. For homologous recombination, plasmid p426_16A_D was amplified using the primer pair dDNA-CS5-F and dDNA-CS5-R as donor DNA for CRISPR-Cas9-based genomic integration (Table 1). To overcome inefficiencies associated with genomic integration, PCR products constructed using the primer pair dDNA-CS5-F and dDNA-CS5-R were amplified once again by PCR using the primer pair CS5+60_F and CS5+60_R to increase a homology region to 120-bp (Table 1). In a yeast transformation process, 1 μg of Cas9-NAT, 20 μg of 16A-D-CS5, and 2 μg of p42K_CS5 were added to *Saccharomyces boulardii* and transformed using the PEG-LiAc method. Verification of genomic integration was performed by yeast colony PCR using the primer pair Conf-CS5-F and Conf-CS5-R (Table 1).

TABLE 1

List of primers used in the invention

| Primer | Sequence (5' →3', restriction sites are underlined) |
|---|---|
| gHIS3_F | TCCACCTAGCGGATGACTCT |
| gHIS3_R | TGCATTACCTTGTCATCTTC |
| dDNA_HIS3_F | GTAAAGCGTATTACAAATGAAACCAAGATTCAGATTGCG ATCTCTTTAAAGGGTTAACCC |
| dDNA_HIS3_R | TTCTGGGAAGATCGAGTGCTCTATCGCTAGGGGTTAACC CTTTAAAGAGATCGCAATCTG |
| 16A_W/OSP_ F_SpeI | ATA ACTAGTGCAGAAAATTTAAATAATAAATCATACGAGTG |
| 16A_W/OSP_ R_XhoI | ATA CTCGAGTTCTTCTGGGACCAGTGTATAAAC |
| 16A_CL_F_ SpeI | ATA ACTAGTATGAGGTCTTTGCTAATCTTGGTGCTTTGCTTCC TGCCCCTGGCTGCTCTGGGGGCAGAAAATTTAAATAATA AATCATAC |
| 16A_CL_R_XhoI | ATA CTCGAGTTCTTCTGGGACCAGT |
| αMF_F_SpeI | ATA ACTAGTATGAGATTTCCTTCAATTTTTACTG |
| αMF_R_16A | GCA GAA AAT TTA AAT AAT AAA GCT TCA GCC TCT CTT TTC T |
| 16A_F_aMF | GAG AAA AGA GAG GCT GAA GCT GCA GAA AAT TTA AAT AAT AAA TCA TAC G |
| 16A_R_αMF_ BamHI | ATA GGATCCTTCTTCTGGGACCAGTGTAT |
| STA1_F_EcoRI | ATA GAATTCATGGTAGGCCTCAAAAATC |

TABLE 1-continued

| List of primers used in the invention | |
|---|---|
| Primer | Sequence (5' →3', restriction sites are underlined) |
| STA1_16A_R | GCA GAA AAT TTA AAT AAT AAA TCA TAC GAG TTT TTT CTG TCG CTG GAG C |
| 16A_STA1_F | GGC TCC AGC GAC AGA AAA AAG CAG AAA ATT TAA ATA ATA AAT CAT ACG AG |
| 16A_R_XhoI | ATA CTCGAGTTCTTCTGGGACCAGTGTAT |
| 16A_SED1_F_SpeI | ATA ACTAGTATGAAATTATCAACTGTCCTATTATCTGCCGGTT TAGCCTCGACTACTTTGGCCCAAGCAGAAAATTTAAATA ATAAATCA |
| 16A_SED1_R_XhoI | ATA CTCGAGTTCTTCTGGGACCAG |
| dDNA-CS5-F | AAA AGA GAA GAA AAA AGA GAA GAA ATG AAT TCT ATT ATG ATA GCG AAT GCA ATT AAC CCT CAC TAA AGG GA |
| dDNA-CS5-R | TGC TGG TTG CCT TAT TAA TTT ATA TGG AAG ACG AGA TAA TTC ATT AAT TAG TAA TAC GAC TCA CTA TAG GGC |
| dDNA-CS5+60_F | ATG GTA CAC GCT CTT GGC AAC ATT GAA ATT ACA GCT CTC ATA TAT AAA AAA TGG AAA GAA AAA AGA GAA GAA AAA AGA GAA GAA ATG AAT |
| dDNA-CS5+60_R | GGC ATA ACA ATA GCG CAC AGA TCC GCA GGT TTC GTA ATA CGC TTA ACA ATA GGC GTC TCC TGC TGG TTG CCT TAT TAA TTT ATA TGG AAG |
| gCS5_F | CTG GTA GTT GCA CAG AAA GAG TTT TAG AGC TAG AAA TAG CAA G |
| gCS5_R | TCT TTC TGT GCA ACT ACC AGC GAT CAT TTA TCT TTC ACT GCG |
| Conf-CS5-F | AAT GAA TTC TAT TAT GAT AGC GAA TGC |
| Conf-CS5-R | CAC AGG ATT TAC GAA GAC C |

TABLE 2

| List of plasmids used in the invention | | |
|---|---|---|
| Plasmid | Description | Reference |
| pRS42H | 2μ origin | EUROSCARF |
| p42H_gHIS3 | pRS42H carrying HIS3 disruption gRNA cassette | This study |
| pRS426GPD | URA3, GPD promoter, CYC1 terminator, 2μ origin, and Amp | (Mumberg et al., 1995) |
| p426_Bp_W/OSP | pRS426GPD harboring BpGH16A from *B. plebeius*, deletion signal peptide | This study |
| p426_Bp_CL | pRS426GPD harboring BpGH16A and chicken lysozyme signal peptide | This study |
| p426_Bp_αMF | pRS426GPD harboring BpGH16A and α-mating factor signal peptide | This study |
| p426_Bp_STA1 | pRS426GPD harboring BpGH16A and STA1 signal peptide | This study |
| p426_Bp_SED1 | pRS426GPD harboring BpGH16A and SED1 signal peptide | This study |
| Cas9-NAT | p414-TEF1p-Cas9-CYC1t-NAT1 | (Zhang et al., 2014) |
| pRS42K | 2μ origin, KanMX | (Taxis & Knop, 2006) |
| p42K_CS5 | pRS42K, gRNA cassette targeting the intergenic site on Chr XV | This study |
| 16A-D-CS5 | BpGH16A, SED1 signal peptide, donor DNA for CS5 site integration | This study |

TABLE 3

List of strains used in the invention

| Strain | Description | Reference |
|---|---|---|
| *S. boulardii* | ATCC MYA-796 | ATCC |
| SB-TU | *S. boulardii*; TRP1 and URA3 disruption | (Liu et al., 2016) |
| SB-HTU | *S. boulardii*; HIS3, TRP 1, and URA3 disruption | This study |
| SB-HTU_16A_E | SB-HTU; pRS426GPD | This study |
| SB-HTU_16A_W | SB-HTU; BpGH16A, deletion signal peptide, pRS426GPD | This study |
| SB-HTU_16A_C | SB-HTU; BpGH16A, chicken lysozyme signal peptide, pRS426GPD | This study |
| SB-HTU_16A_A | SB-HTU; BpGH16A, a-mating factor signal peptide, pRS426GPD | This study |
| SB-HTU_16A_S | SB-HTU; BpGH16A, STA1 signal peptide, pRS426GPD | This study |
| SB-HTU_16A_D | SB-HTU; BpGH16A, SED1 signal peptide, pRS426GPD | This study |
| SB_16A_D | *S. boulardii*; BpGH16A, SED1 signal peptide | This study |

Example 2: Cell Culture Conditions

To produce neoagarooligosaccharides from the strain *Saccharomyces boulardii* prepared according to Example 1, 2.5 g/L of agarose was provided as a substrate at a temperature of 37° C. and fermentation was performed at 200 rpm in a 125-mL flask for 72 hours. To prevent coagulation of agarose during fermentation, agarose (Sigma-Aldrich) with a low gelation temperature was used. First, strains SB-HTU_16A_C, SB-HTU_16A_A, SB-HTU_16A_S, and SB-HTU_16A_D were cultured in yeast synthetic complete (YSC) medium at 37° C. and 200 rpm. Pre-cultured cells were centrifuged at 10,170×g for 10 minutes and washed twice with sterile distilled water, and harvested cells were inoculated into 20 mL of YSC medium containing 20 g/L of glucose and 2.5 g/L of agarose in 50 mM KHP buffer (pH 5.5). The initial cell density was inoculated at an optical density 600 nm ($OD_{600}$) of 1.0. As a control, fermentation of strains SB-HTU_16A_E and SB-HTU_16A_W was also performed under the same conditions.

Example 3: Method of Quantifying Neoagarooligosaccharides Through Cell Growth Measurement and HPLC Analysis Cell growth was measured by measuring $OD_{600}$ using a UV-visible spectrophotometer (Bio-Rad, Hercules, CA, USA). HPLC analysis was performed to analyze and quantify the reaction products of *Saccharomyces boulardii* and agarose, including neoagarotetraose, glucose, acetic acid, and ethanol. The column used during analysis was an Aminex HPX-87H column (Bio-Rad), which was equipped with a refractive index (RI) detector. The column and RI detector temperatures were set at 65° C. and 55° C., respectively, and the column used 0.005 M sulfuric acid as a mobile phase at a flow rate of 0.5 mL/min.

Example 4: Method of Confirming Fermentation Products Through TLC Analysis

Thin layer chromatography (TLC) analysis was performed to identify the hydrolysis products of agarose during fermentation. For each time point (0, 12, 24, 36, 48, and 72-h) during fermentation, 1 mL of cell culture including fermentation products was obtained. For accurate measurements, the resulting cell culture was boiled to terminate further enzymatic reactions. After centrifugation at 16,609×g for 15 minutes at 4° C., 1 μL of each supernatant was loaded onto a silica gel 60 plate (Merck, Damstadt, Germany). After drying the TLC plate, it was visualized using a solution of 10% (v/v) sulfuric acid in ethanol and a solution of 0.2% (w/v) naphthoresorcinol in ethanol sequentially (Yun E. J., et al. (2013) Appl Microbiol Biotechnol. 97, 2961-2970).

Example 5: Confirmation of Neoagarotetraose Production Using *Saccharomyces boulardii*

Figure 2:
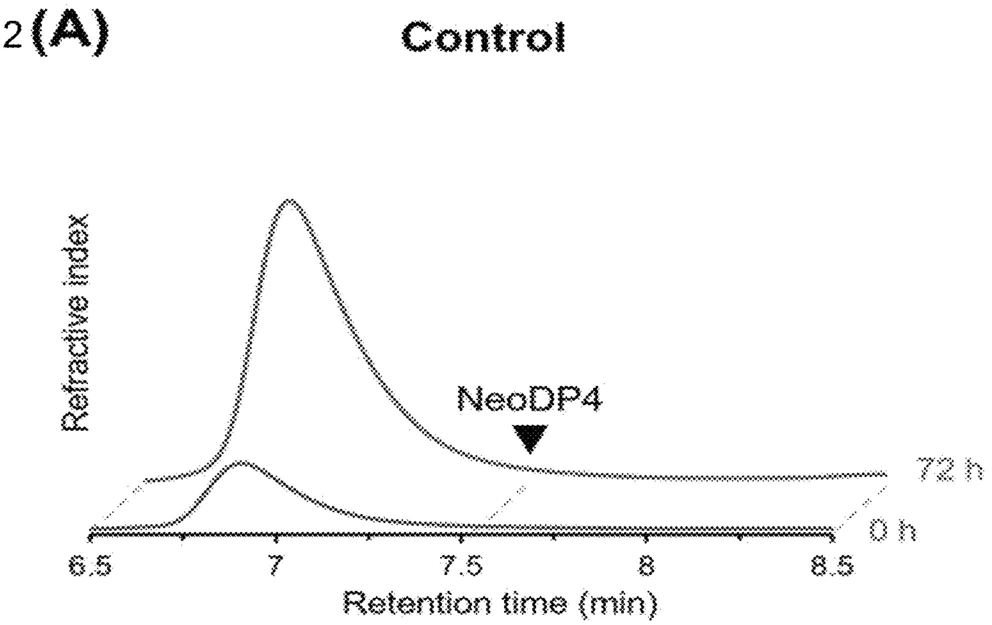
FIG. 2(A) and FIG. 2(B) the results of confirming the fermentation product using a strain (SB-HTU_16A_C) into which the BpGH16A gene was introduced using HPLC. Fermentation was performed at 37° C. for 72 hours using 2.5 g/L of agarose as a substrate. FIG. A(A) is the result of fermentation product analysis using a wild-type strain as a control group.
Figure 2:
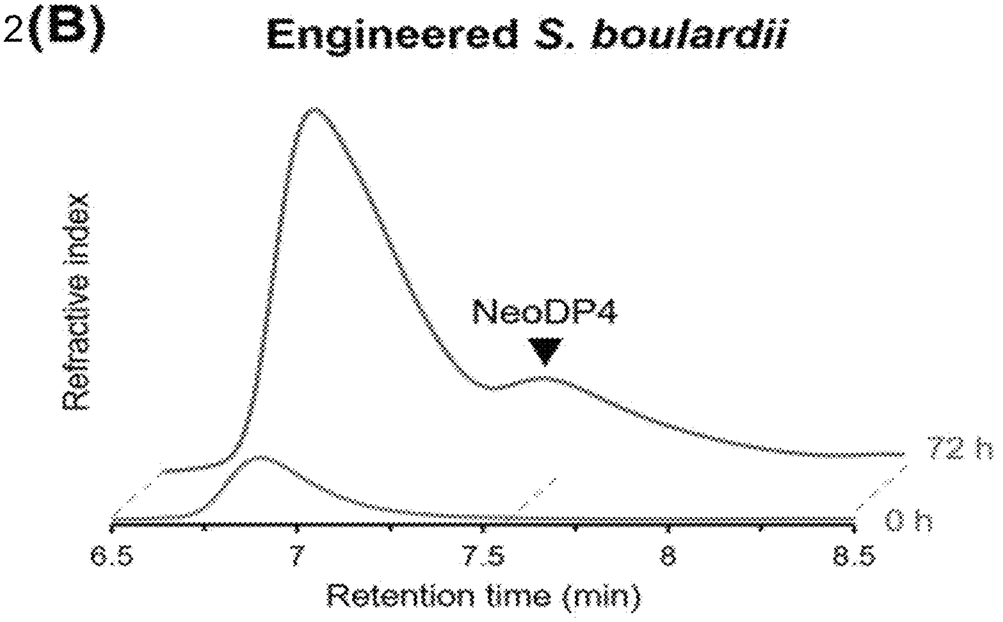

In order to produce neoagarotetraose using engineered yeast, secretion of beta-agarose, which enables agarose decomposition, is required in yeast. Therefore, the expression and secretion of endo-type beta-agarase BpGH16A by *Saccharomyces boulardii* were first tested. For testing, strain SB-HTU_16A_C was used, in which the chicken lysozyme signal peptide (CL), which was previously demonstrated to function in *Saccharomyces boulardii* (Liu J-J., et al. (2016) Appl Environ Microbiol. 82, 2280-2287), was introduced. In HPLC analysis of a SB-HTU_16A_C fermentation product, a peak was detected at a retention time of 7.6 minutes corresponding to neoagarotetraose (FIG. 2A and 2B). In contrast, no peak was detected in the product of the control strain SB-HTU_16A_E including an empty vector. Therefore, these results confirmed that BpGH16A is functionally expressed, secreted from *Saccharomyces boulardii*, and produced neoagarotetraose by hydrolyzing agarose.

Example 6: Selection of Optimal Signal Peptide to Produce Neoagarotetraose

Figure 3:
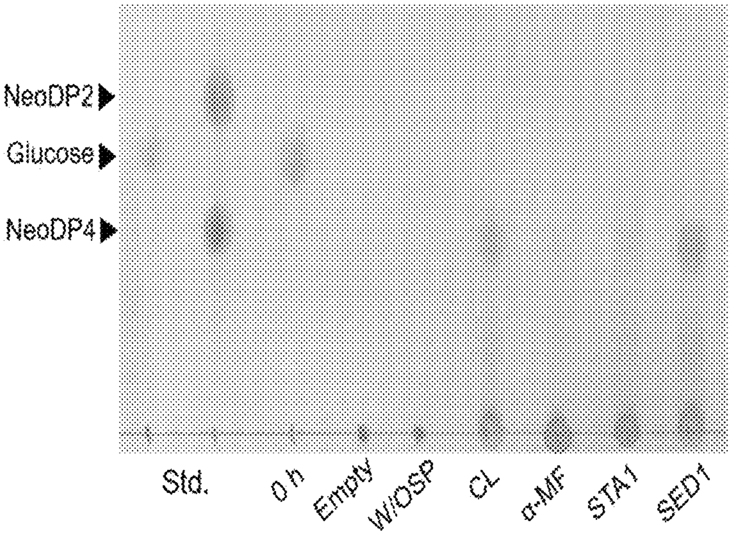
FIG. 3(A) and FIG. 3(B) are the results of comparing the amounts of neoagarotetraose (NeoDP4) produced when strains, in which different signal peptide sequences were introduced in front of the BpGH16A gene, which is a beta-agarase, in *Saccharomyces boulardii* were fermented with agarose. Fermentation was performed at 37° C. for 72 hours using 2.5 g/L of agarose as a substrate.
Figure 3:
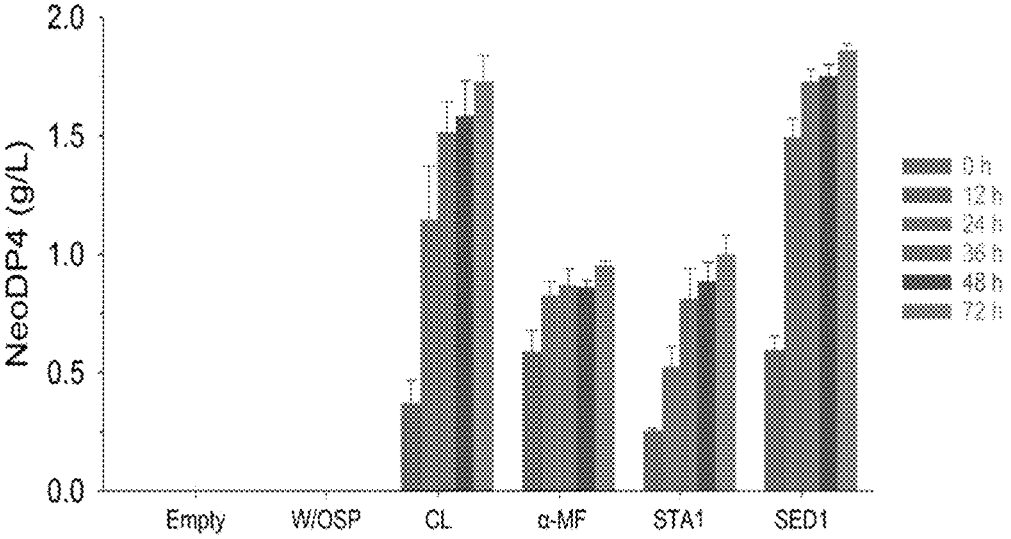

Since the enzyme BpGH16A was confirmed to be expressed and secreted in *Saccharomyces boulardii*, the next step was to find the optimal signal peptide to increase neoagarotetraose production. A total of four types of signal peptides: CL, α-MF, STA1, and SED1 were tested. Each signal peptide was fixed in front of the BpGH16A sequence and introduced into the SB-HTU strain to find the signal peptide that produces the most neoagarotetraose. The production of neoagarotetraose by the engineered yeast was confirmed by TLC analysis after 72 hours of culture (FIG. 3A). As a result, neoagarotetraose was noticeably produced by the strain with CL and SED1, slightly produced by the strain with STA1, and weakly detected in the strain with α-MF. To accurately compare the amount of neoagarotetraose generated by each engineered yeast, HPLC analysis was performed (FIG. 3B). As a result, neoagarotetraose was found to gradually increase as the 72-hour culture for each strain progressed, and the strain including SED1 produced the largest amount of neoagarotetraose. The amount of neoagarotetraose generated after 72 hours of fermentation was 1.73, 0.95, 0.99, and 1.86 g/L when signal peptides, namely CL, α-MF, STA1, and SED1, were used, respectively. Therefore, *Saccharomyces cerevisiae*-derived SED1, which produces the highest amount of neoagarotetraose, was selected as the optimal signal peptide for neoagarotetraose production.

Although neoagarotetraose was generated in all groups to which the signal peptide was attached, it was not generated in two control groups (FIG. 3A and 3B). In particular, SB-HTU_16A_W, used as one of the negative controls, is a strain created to confirm that the extracellular activity of BpGH16A is derived from secretion by a heterologously expressed signal peptide rather than cell lysis. Since neoagarotetraose was not detected in the culture fluid of SB-HTU_16A_W, it was confirmed that agarose was decomposed to neoagarotetraose by BpGH16A secreted outside the cells. Since there has been no report on the comparison of signal peptides in *Saccharomyces boulardii* so far, there is a possibility that the present invention may be used in the field of protein production and secretion by *Saccharomyces boulardii.*

Example 7: Fermentation to Produce Neoagarotetraose Using Improved Strains

Based on the signal peptide selection results, strain SB-HTU_16A_D including the SED1 signal peptide was cultured. Fermentation was performed for 72 hours in YSC medium containing 2.5 g/L of agarose and without uracil. Neoagarotetraose production was confirmed by TLC analysis (FIG. 4A). It was confirmed that the initially added glucose was depleted after 36 hours. As a result of analyzing the fermentation products at each time point by HPLC, 1.86 g/L of neoagarotetraose was produced after 72 hours of fermentation (FIG. 4B). Cell growth entered a stationary phase at 24 hours and reached $OD_{600}$=6.7 after 72 hours. Both ethanol and acetic acid were accumulated at 4.8 g/L. In conclusion, neoagarotetraose was produced as the target primary product by engineered yeast SB-HTU_16A_D.

Example 8: Strain Production and Fermentation Using CRISPR-Cas9 Technology

Figure 5:
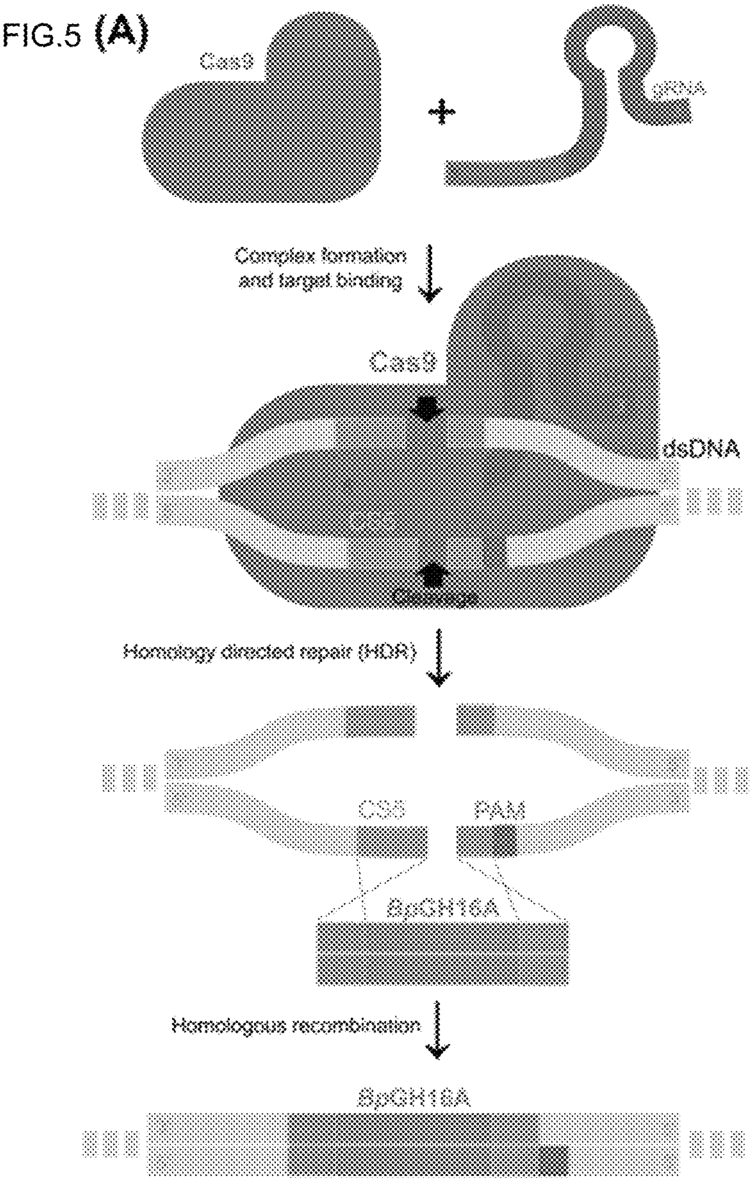
FIG. 5(A) and FIG. 5(B) relate to a method of preparing *Saccharomyces boulardii*, which can produce neoagarooligosaccharides, using CRISPR-Cas9 technology.
Figure 5:
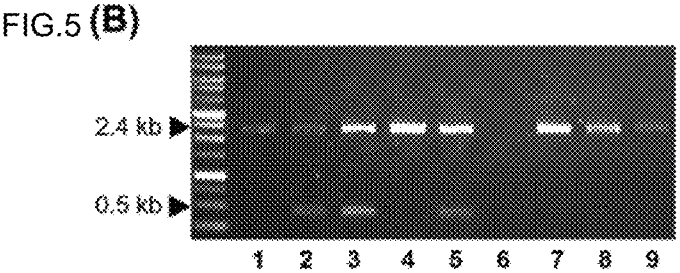

The use of genomic integration technologies, such as the CRISPR-Cas9 system, can avoid problems that may occur in complex intestinal environments when using plasmids. These problems include plasmid instability in the absence of selective pressure, potential spread to other microorganisms, and increased metabolic burden associated with the maintenance of multicopy plasmids (Durmusoglu D., et al. (2020) bioRxiv. 915389). In the present invention, BpGH16A was introduced into the genome of *Saccharomyces boulardii* along with SED1 for stable expression of the enzyme. BpGH16A gene insertion was performed by CRISPR-Cas9-based homologous recombination (FIG. 5A). Successful insertion of the BpGH16A gene after yeast transformation was confirmed by yeast colony PCR. A primer pair Conf-CS5-F and Conf-CS5-R was designed and used to cover 2.4-kb when the gene was inserted, and 0.5-kb when the gene was not inserted (Table 2). Successful integration of BpGH16A and SED1 into *Saccharomyces boulardii* was confirmed by the formation of a 2.4-kb single band in lanes 4, 7, and 8 when yeast colony PCR was performed (FIG. 5B).

Figure 6:
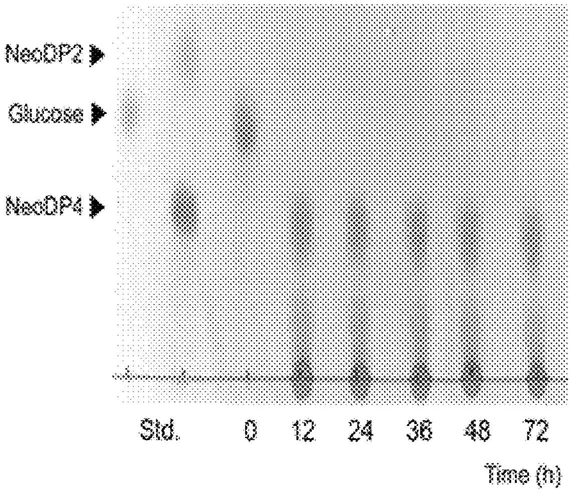
FIG. 6A and FIG. 6B shows the results of confirming the materials and cell growth produced over time when agarose was provided as a substrate using *Saccharomyces boulardii* (SB_16A_D) engineered using CRISPR-Cas9 technology and fermentation was performed for 72 hours.
Figure 6:
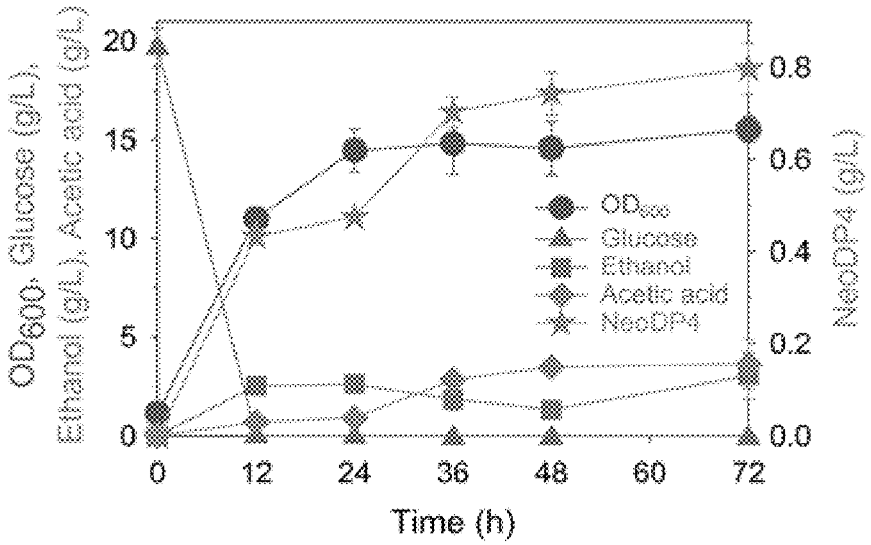

Finally, the SB_16A_D strain including BpGH16A and SED1 was constructed in the *Saccharomyces boulardii* genome using CRISPR-Cas9, and flask fermentation was performed for 72 hours in a YSC medium including 2.5 g/L of agarose. Neoagarotetraose production was confirmed by TLC analysis (FIG. 6A), suggesting that BpGH16A was secreted from strain SB 16A_D. For more accurate fermentation product analysis, HPLC analysis and growth measurements were also performed at each time point (FIG. 6B). Glucose was depleted before 12 hours of incubation, and the strain grew to $OD_{600}$=15.51 in 72 hours. After fermentation, 0.80 g/L of neoagarotetraose was produced, and 3.03 g/L of ethanol and 3.65 g/L of acetic acid were accumulated.

Compared to using a plasmid vector system with an auxotrophic marker, the final $OD_{600}$ after 72 hours of fermentation of the strain constructed with the CRISPR-Cas9 system was 2.3 times higher, but neoagarotetraose production was lower. The reason for this difference is estimated to be the relatively strong promoter and high copy number of the pRS426GPD plasmid (Mumberg D., et al. (1995) Gene. 156, 119-122). Nevertheless, the successful protein secretion of *Saccharomyces boulardii* constructed by genomic integration demonstrated the potential of *Saccharomyces boulardii* to be used as a microbial cell factory to produce useful proteins and substances in the human intestines.

The present invention presents a process of preparing a recombinant yeast that can produce neoagarooligosaccharides by decomposing agarose. In other words, it was found that neoagarooligosaccharides can be produced using agarose as a substrate using *Saccharomyces boulardii* produced through the present invention. This can be utilized to produce useful substances in the intestines, including prebiotics, using *Saccharomyces boulardii*, which is a probiotic yeast, and to develop recombinant enzymes.

What is claimed is:

1. A synbiotic composition comprising a Recombinant *Saccharomyces boulardii* transformed with a gene encoding beta-agarase and agarose as a substrate, wherein the beta-agarase gene is represented by SEQ ID NO: 1, wherein neoagarooligosaccharides are produced from the agarose by the beta-agarase expressed by the recombinant *Saccharomyces boulardii*, and wherein the recombinant *Saccharomyces boulardii* functions as a probiotic and the neoagarooligosaccharides function as a prebiotic.

2. The synbiotic composition of claim 1, wherein the recombinant *Saccharomyces boulardii* is transformed with a gene encoding a signal peptide that secretes the beta-agarase enzyme outside the recombinant *Saccharomyces boulardii*.

3. The synbiotic composition of claim 2, wherein the signal peptide is one or more of a chicken lysozyme signal peptide (CL), a *Saccharomyces cerevisiae*-derived β-binding factor signal peptide (β-MF), a *Saccharomyces diastaticus*-derived STA1 signal peptide (STA1), and a *Saccharomyces cerevisiae*-derived SED1 signal peptide (SED1).

4. The synbiotic composition of claim 3, wherein the chicken lysozyme signal peptide (CL) is represented by SEQ ID NO: 2, the *Saccharomyces cerevisiae*-derived α-binding factor signal peptide (α-MF) is represented by SEQ ID NO: 3, the *Saccharomyces diastaticus*-derived STA1 signal peptide (STA1) is represented by SEQ ID NO: 4, and the *Saccharomyces cerevisiae*-derived SED1 signal peptide (SED1) is represented by SEQ ID NO: 5.

5. The synbiotic composition of claim 1, wherein transformation is achieved by CRISPR-Cas9 or a recombinant vector.

6. The synbiotic composition of claim 1, further comprising probiotics.

* * * * *